US011103377B1

(12) United States Patent
Weston

(10) Patent No.: US 11,103,377 B1
(45) Date of Patent: Aug. 31, 2021

(54) IRISING DRAINAGE DEVICE AND IRISING RECTAL CATHETER

(71) Applicant: LUMOPOL, LLC, Harrisburg, PA (US)

(72) Inventor: David M. Weston, Quarryville, PA (US)

(73) Assignee: LUMOPOL, LLC, Harrisburg, PA (US)

( * ) Notice: Subject to any disclaimer, the term of this patent is extended or adjusted under 35 U.S.C. 154(b) by 0 days.

(21) Appl. No.: 17/218,370

(22) Filed: Mar. 31, 2021

(51) Int. Cl.
*A61F 5/451* (2006.01)
*A61M 1/00* (2006.01)
*A61M 25/00* (2006.01)
*A61B 17/221* (2006.01)

(52) U.S. Cl.
CPC ............... *A61F 5/451* (2013.01); *A61M 1/87* (2021.05); *A61B 17/221* (2013.01); *A61M 2025/0024* (2013.01)

(58) Field of Classification Search
CPC .... A61M 3/0291; A61M 3/02; A61M 3/0295; A61M 2210/1064; A61M 2025/0024; A61M 1/87; A61M 1/0023; A61M 1/90; A61F 5/451; A61B 17/221; A61B 2017/2212–2217
See application file for complete search history.

(56) References Cited

U.S. PATENT DOCUMENTS

| 2,667,117 A | 1/1954 | Millard et al. |
| 3,815,608 A | 6/1974 | Spinosa et al. |
| 4,553,533 A | 11/1985 | Leighton |
| 4,668,225 A | 5/1987 | Russo et al. |
| 5,080,650 A | 1/1992 | Hirsch et al. |
| 6,039,714 A | 3/2000 | Cracauer et al. |
| 6,248,096 B1 | 6/2001 | Dwork et al. |

(Continued)

OTHER PUBLICATIONS

Popek et al., "Indwelling Rectal Tubes: An Unusual Cause of Significant Rectal Bleeding in Two Critically Ill Patients," The American Surgeon, Feb. 2013, p. 219-220, vol. 79.

(Continued)

*Primary Examiner* — Susan S Su
(74) *Attorney, Agent, or Firm* — McNees Wallace & Nurick LLC

(57) ABSTRACT

An irising drainage device is disclosed, including an irising collection funnel having a plurality of overlapping petals extending from an annulus defining a central aperture and a conduit extending from the annulus away from the irising collection funnel. The conduit includes a lumen in fluid communication with the central aperture. An irising rectal catheter is disclosed, including an irising collection funnel having a plurality of overlapping elastically deformable petals extending from an annulus defining a central aperture and an elastomeric tube extending from the central aperture away from the irising collection funnel. The elastomeric tube includes a lumen in fluid communication with the central aperture. The irising collection funnel is configured to elastically narrow in response to a radially inward pressure and expand with reduction of the radially inward pressure. The plurality of elastically deformable overlapping petals, the annulus, and the elastomeric tube are integrally formed with one another.

20 Claims, 13 Drawing Sheets

(56) References Cited

U.S. PATENT DOCUMENTS

| | | |
|---|---|---|
| 6,322,538 B1 | 11/2001 | Elbert et al. |
| 6,576,429 B1 | 6/2003 | Hällgren |
| 6,743,198 B1 | 6/2004 | Tihon |
| 7,147,627 B2 | 12/2006 | Kim et al. |
| 7,722,583 B2 | 5/2010 | Kim et al. |
| 8,070,736 B2 | 12/2011 | Nishtala et al. |
| 8,075,539 B2 | 12/2011 | Nishtala et al. |
| 8,323,255 B2 | 12/2012 | Martino et al. |
| 8,597,266 B2 | 12/2013 | Nishtala et al. |
| 8,777,912 B2 | 7/2014 | Nishtala et al. |
| 8,801,683 B2 | 8/2014 | Kim et al. |
| 8,926,577 B2 | 1/2015 | Nishtala et al. |
| 9,492,227 B2 | 11/2016 | Lopes et al. |
| 10,603,204 B2 | 3/2020 | Laniado |
| 2005/0004471 A1 | 1/2005 | Hogendijk et al. |
| 2007/0225642 A1 | 9/2007 | Houser et al. |
| 2009/0306600 A1 | 12/2009 | Regnault |
| 2011/0077680 A1* | 3/2011 | Heuser ............... A61B 17/221 606/200 |
| 2013/0261638 A1* | 10/2013 | Diamant ............ A61M 1/0023 606/113 |
| 2015/0011955 A1 | 1/2015 | Sharma et al. |
| 2017/0296795 A1* | 10/2017 | Troutman ......... A61M 25/1002 |

OTHER PUBLICATIONS

Daniel et al. "Rectal bleeding post the use of the Flexi-Seal Faecal management system," Royal Australasian College of Surgeons, 2018, p. E83-E84.

Reynolds et al. "A case of pressure ulceration and associated haemorrhage in a patient using a faecal management system," Australian College of Critical Care Nurses, Feb. 2012, p. 188-194, vol. 25, Elsevier.

Sparks et al. "Recal Trauma and Associated Hemorrhage With the Use of the ConvaTecFlexi-Seal Fecal Management System: Report of 3 Cases," Diseases of the Colon & Rectum, 2010, p. 346-349, vol. 53.

Mulhall et al. "Massive Gastrointestial Hemorrhage as a Complication of the Flexi-Seal Fecal Management System," American Journal of Critical Care, Nov. 2013, p. 537-543, vol. 22 No. 6.

Tiwari et al. "The Traumatic Tube: Bleeding Rectal Ulcer Caused by Flexi-Seal Device," Case Reports in Gastrointestinal Medicine, vol. 2017, article ID 5278971.

"BD Dignishield," https://www.youtube.com/watch?v=TJ1pxMbxBKQ, posted Oct. 30, 2020.

DigniShield, "Stool Management System," brochure, Bard Medical, 2010.

DigniShield, "Stool Management System," brochure, Bard Medical, 2012.

"DigniShield Stool Management System," https://vimeo.com/362647060, accessed Feb. 11, 2021.

Page et al. "Significant Rectal Bleeding as a Complication of a Fecal Collecting Device: Report of a Case," Diseases of the Colon & Rectum, 2008, p. 1427-1429, vol. 51.

Ousey, "An Easily Forgotten Tube," Patient Safety Network, https://psnet.ahrq.gov/web-mm/easily-forgotten-tube#, Feb. 2014.

* cited by examiner

IRISING DRAINAGE DEVICE AND IRISING RECTAL CATHETER

FIELD OF THE INVENTION

This application is directed to irising drainage devices. More specifically, this application is directed to irising drainage devices having irising collection funnels incorporating overlapping petals.

BACKGROUND OF THE INVENTION

Much of what maintains a healthy digestive tract is a healthy biome, an environment of friendly bacteria. If the biome is destroyed through unfriendly invaders or through destruction of this friendly bacteria by antibiotics (as may be prescribed to fight disease elsewhere in the body), the excretory system ceases to function, namely in that the water is not reabsorbed into the circulatory system. This condition, known as diarrhea, may be caused by numerous underlying conditions, such as, but not limited to, infectious diseases (e.g., cholera), complications of previous treatment of other diseases (e.g., Clostridia *Difficile*), loss of bowel control (e.g., aging or stroke), autoimmune diseases (e.g., chronic ulcerative colitis or Crohn's Disease), previous surgeries (e.g., short bowel syndrome), food allergies or intolerances (e.g., gluten enteropathy or lactase enzyme deficiency), or trauma.

Diarrhea is a pervasive affliction. According to the World Health Organization, in 2016 there were 132,121 cases of cholera. According to the United States Center for Disease Control, in 2015 there were approximately 500,000 cases of *C. difficile*, with a mortality rate of 15% for those cases hospitalized for 30 days or more, resulting in approximately 29,000 fatalities. Among 16,000 nursing homes and 5,700 hospitals in the U.S., many patients who are elderly and/or suffering from dementia are unable to contain stool excretion. While the causes are diverse and numerous, diarrhea, a condition in which the excretory system ceases to function such that water is not reabsorbed into the circulatory process, is widespread and leads to significant fatalities across the globe.

Ongoing uncontrolled diarrhea is often a fatal condition, particularly in resource-limited environments. Uninterrupted loss of fluid may lead to fatal dehydration if fluid loss cannot be quantified and replaced appropriately. Continual wiping, in the effort to maintain cleanliness, eventually causes open abrasions. Moreover, chronic diarrhea is deeply corrosive to the anus, easily leading to infection. Digestive enzymes are designed to function within the body; when continually seeping to the outside, digestive enzymes will corrode external skin, which is of a different composition than internal mucosa and is an area these enzymes were never meant to touch. Anal corrosion creates open fissures and sores, exacerbated by wiping in effort to maintain cleanliness. This vicious circle increases infection risk and is quite painful for the patient. It also places significant additional care burdens on nursing staff. Further, uncontrolled diarrhea, particularly where a person is in a weakened state due to illness and dehydration, such as during epidemic conditions, may lead to sanitation issues affecting more than just the person afflicted with diarrhea.

Medications are often useful for controlling diarrhea but have side effects. The most effective are opioids, which may be addictive. Bulk agents may make things worse.

Antispasmodics may lead to toxic megacolon. Antibiotics to treat certain infections may lead to secondary infection with *C. difficile*. In cases of infection with *C. difficile*, the transplanting of another healthy person's stool into the colon of the diseased one to restore the human biome may be required in some extreme cases. However, this complicated procedure is difficult to access in less developed countries.

When these solutions do not work or are not feasible, especially in less-developed locations, a rectal tube may the best option, either as a facilitator to ultimate recovery or a stop-gap before colostomy surgery. The rectal tube is able to meet short- and long-term needs of containing diarrhea and may quantify the fluid being excreted, which must be replaced for life sustenance during the acute phases of chronic diarrhea.

Recognizing the need for a rectal tube, modern science first attempted using a Foley catheter. Designed in 1929, this catheter was originally created only for drainage from the human urinary bladder. The Foley catheter contains an expandable balloon on the proximal end. The tube with flaccid balloon is placed through the urethra and into the bladder, and once inside the bladder, the balloon is expanded to keep the tube from falling out. Side holes in the tube allow urine to flow into the tube and out of the body into a bag. The catheter may remain in the body for significant periods of time. However, as a rectal device, the size of the catheter is hardly large enough to contain the flow or consistency of diarrhea effluent; the largest Foley catheter reaches a maximum 24 or 26 French units (millimeters circumference), about the size of a pencil. A balloon keeps the tube in place, but the diarrhea cannot travel down the tube.

Until about 2000, there were no practical solutions other than a simple tube (like a hose) in larger sizes of 30 or 40 French, taped to the buttocks or leg of the patient so as to temporarily inhibit a body's natural efforts to expel it. Such tubes always leak, creating sanitary issues and placing digestive juices directly on skin not meant to touch them. Unfortunately, this remains the best available in resource-limited environments such as undeveloped countries where cost and supply problems prevent using current improvements available in more affluent countries. However, because such simple tubes are easily and frequently expelled, and require significant maintenance, when an epidemic, such as cholera, strikes, the patients are usually placed on "cholera cot," mattresses with openings cut through which diarrhea flows, to be collected in buckets. Fluid loss is measured and attempts made to restore this volume by means of orally or intravenously ingested solutions.

Attempts have been made to create rectal tubes using balloons similar in concept to a Foley catheter; however, such devices suffer from numerous deficiencies, including leakage and pressure problems. Fitted balloons snuggly fitting into the rectum with a central orifice to collect effluent for removal are difficult to keep in place. Not only do the body's innate peristatic forces want to expel a snuggly fitted balloon pressing against the rectal wall, but also the brain registers resistance to the sensation of a mass sitting within the rectal vault. Care must be exercised to not distend the balloon beyond 50-60 cc of water because of the defecatory response elicited when the volume approaches 90 cc. Ultimately, such devices do not work in a satisfactory manner. Diarrhea leaks around the rectal tube, and the difficulties typically persist until the patients get better or the caregivers are forced to resort to surgery. Serious complications may arise from use, including pressure sores, bleeding, and infection. Moreover, the cost of such devices may run over $1,000 per unit, which is a prohibitive cost in most regions with the greatest need for a solution.

BRIEF DESCRIPTION OF THE INVENTION

In one exemplary embodiment, an irising drainage device comprises an irising collection funnel including a plurality of overlapping petals extending from an annulus defining a central aperture and a conduit extending from the annulus away from the irising collection funnel. The conduit has a lumen in fluid communication with the central aperture.

In another exemplary embodiment, an irising rectal catheter comprises an irising collection funnel including a plurality of overlapping elastically deformable petals extending from an annulus defining a central aperture and an elastomeric tube extending from the central aperture away from the irising collection funnel. The elastomeric tube has a lumen in fluid communication with the central aperture. The irising collection funnel has a base conformation of the plurality of overlapping petals in the absence of external stimuli and is configured to elastically narrow in response to a radially inward pressure, with the plurality of overlapping petals increasing in overlap with one another, and expand back toward the base conformation with reduction of the radially inward pressure, with the plurality of overlapping petals decreasing in overlap with one another. The plurality of elastically deformable overlapping petals, the annulus, and the elastomeric tube are integrally formed with one another. The plurality of elastically deformable overlapping petals sequentially overlap one another about a periphery of the irising collection funnel. When inserted into a patient, the irising collection funnel conforms spatially to a rectal cavity of the patient, and the elastomeric tube extends from the annulus which is disposed in the rectal cavity through an anus of the patient to an external environment.

BRIEF DESCRIPTION OF THE DRAWINGS

Wherever possible, the same reference numbers will be used throughout the drawings to represent the same parts.

DETAILED DESCRIPTION OF THE INVENTION

Figure 1A:
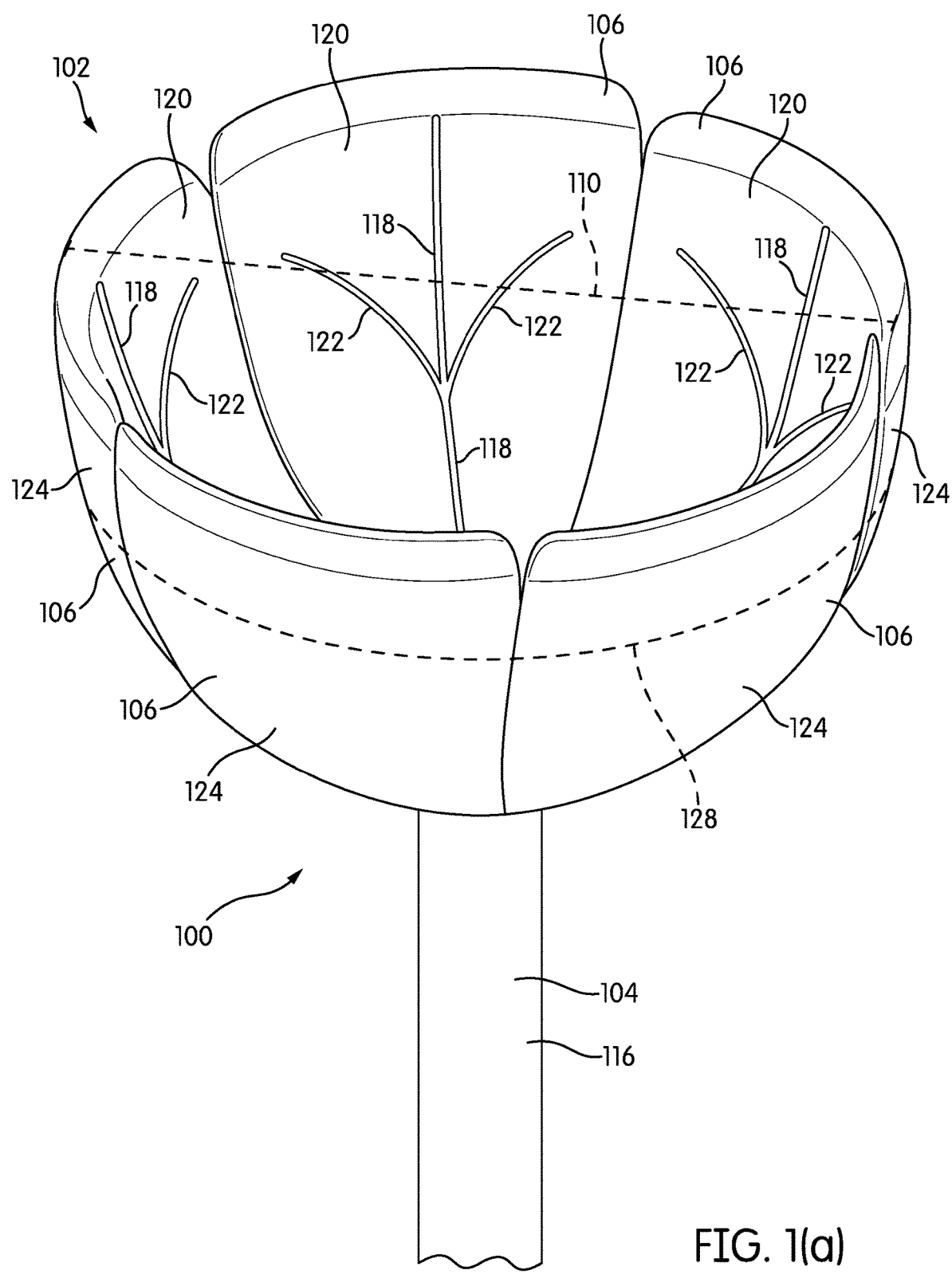
FIG. 1(a) is a perspective view of an irising drainage device in a base conformation, according to an embodiment of the present disclosure.

Embodiments of the present disclosure, in comparison to devices not utilizing one or more features disclosed herein, decrease device costs, decrease device complexity, increase device durability, increase patient comfort, decrease involuntary contractions (peristalsis) of the rectum attempting to expel the device, allow for continuous use for longer periods than prior solutions, potentially even continuous use in excess of thirty days, decrease occurrence of health complications such as rectal mucosal ischemia, necrosis, ulceration, bleeding, and fatal hemorrhage, decrease resistance to removal of the device, or combinations thereof.

Referring to FIGS. 1(a), 1(b), 2(a), 2(b), 2(c), 3(a), and 3(b), in one embodiment, an irising drainage device 100 includes an irising collection funnel 102 and a conduit 104. The irising collection funnel 102 includes a plurality of overlapping petals 106 extending from an annulus 108 defining a central aperture 110. The conduit 104 extends from the annulus 108 in a direction away from the irising collection funnel 102, and the conduit 104 includes a lumen 112 in fluid communication with the central aperture 110. As used herein, "irising" refers to the expansion and contraction of the irising collection funnel 102 (as the plurality of overlapping petals 106 increase and decrease in overlap with one another) as viewed from the top (end on to the irising collection funnel 102 distal from the conduit 104) of the irising collection funnel.

Figure 4A:
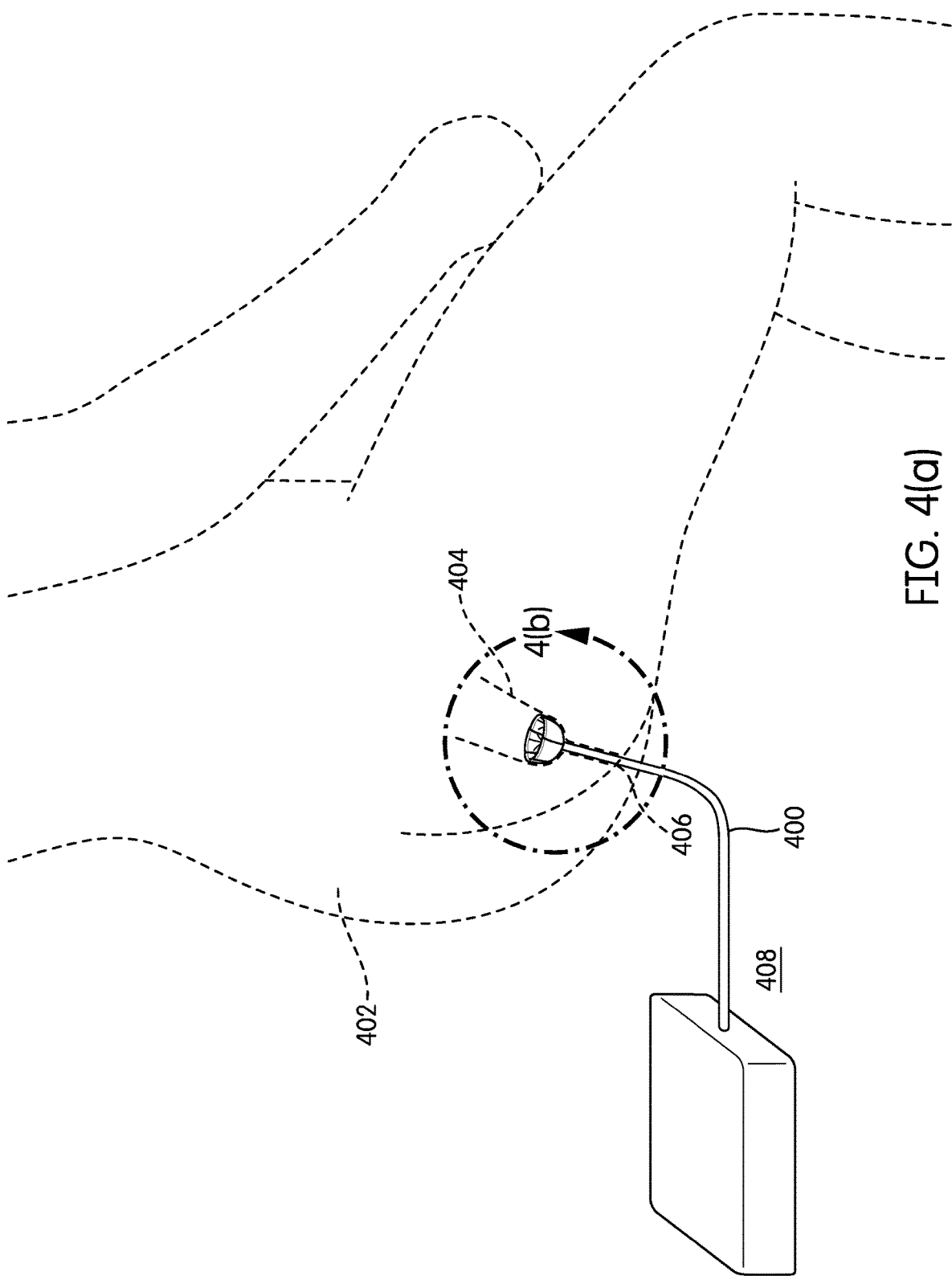
FIG. 4(a) is diagrammatic view of a rectal catheter disposed in a rectum, according to an embodiment of the present disclosure.
Figure 4B:
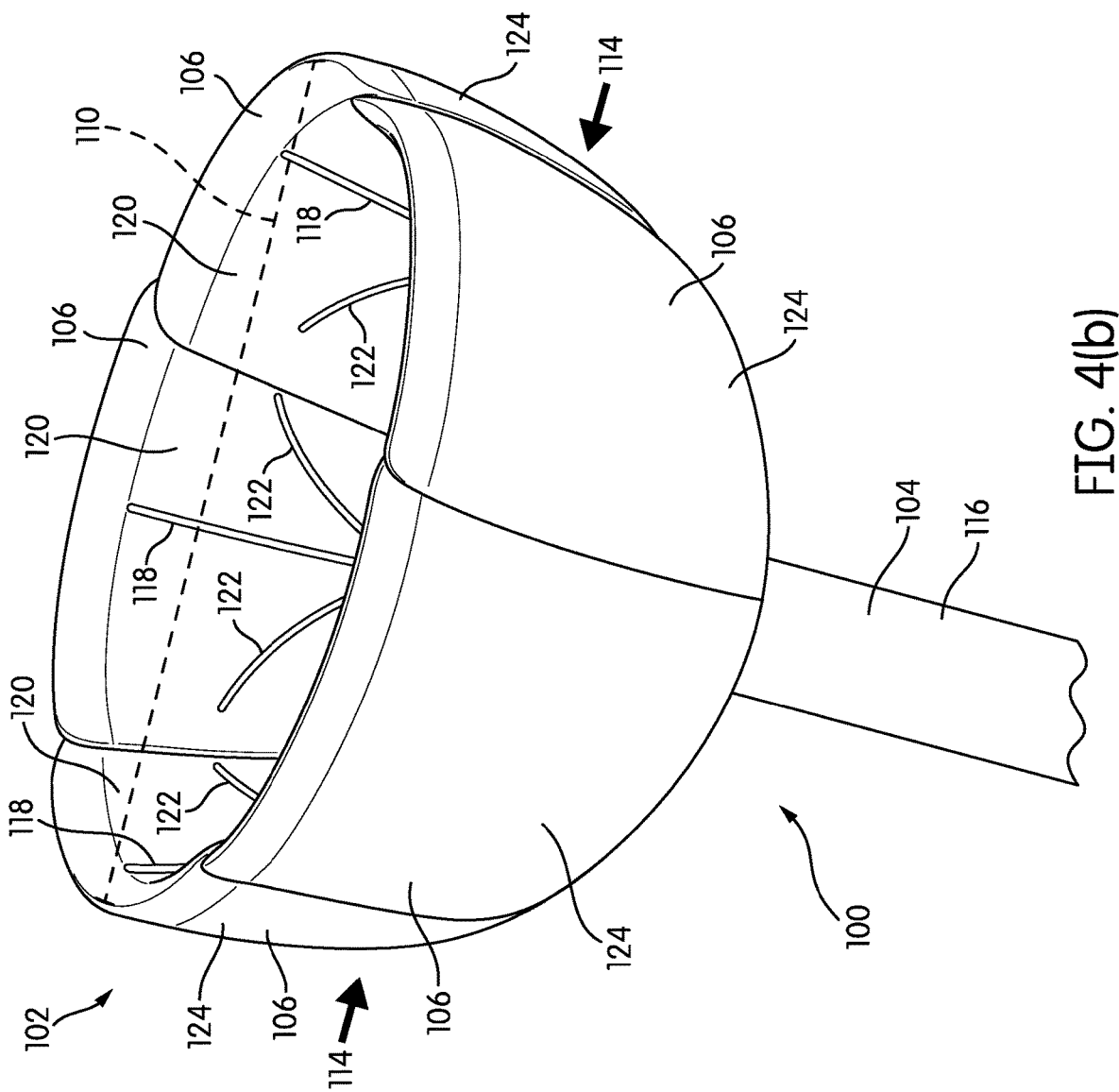
FIG. 4(b) is an expanded view of the rectal catheter of FIG. 4(a) showing deformation of the irising drainage device due to rectal wall pressure, according to an embodiment of the present disclosure.

The irising drainage device 100 may be any suitable device, including, but not limited to, a catheter, a rectal catheter, a colostomy catheter, a surgical drain, or combinations thereof. In one embodiment (as shown in FIG. 4(a)), wherein the irising drainage device 100 is a rectal catheter 400, when inserted into a patient 402, the irising collection funnel 102 conforms spatially to a rectal cavity 404 of the patient 402, and the conduit 104 extends from the annulus 108 which is disposed in the rectal cavity 404 through an anus 406 of the patient to an external environment 408. The irising drainage device 100 may be deformed to an oblong cross-section due to the shape of the rectal cavity 404 (as shown in FIG. 4(b)). In another embodiment, the conduit 104 may extend from one internal environment through an orifice into a different internal environment. The irising drainage device 100 may be used in any human or animal cavity which communicates to another space, whether internal or external, and may be used similarly in non-living systems, such as a tap for a fluid containing vessel. The irising drainage device 100 may be used for removal of fluids having varying viscosities or amounts of solid matter.

Figure 1B:
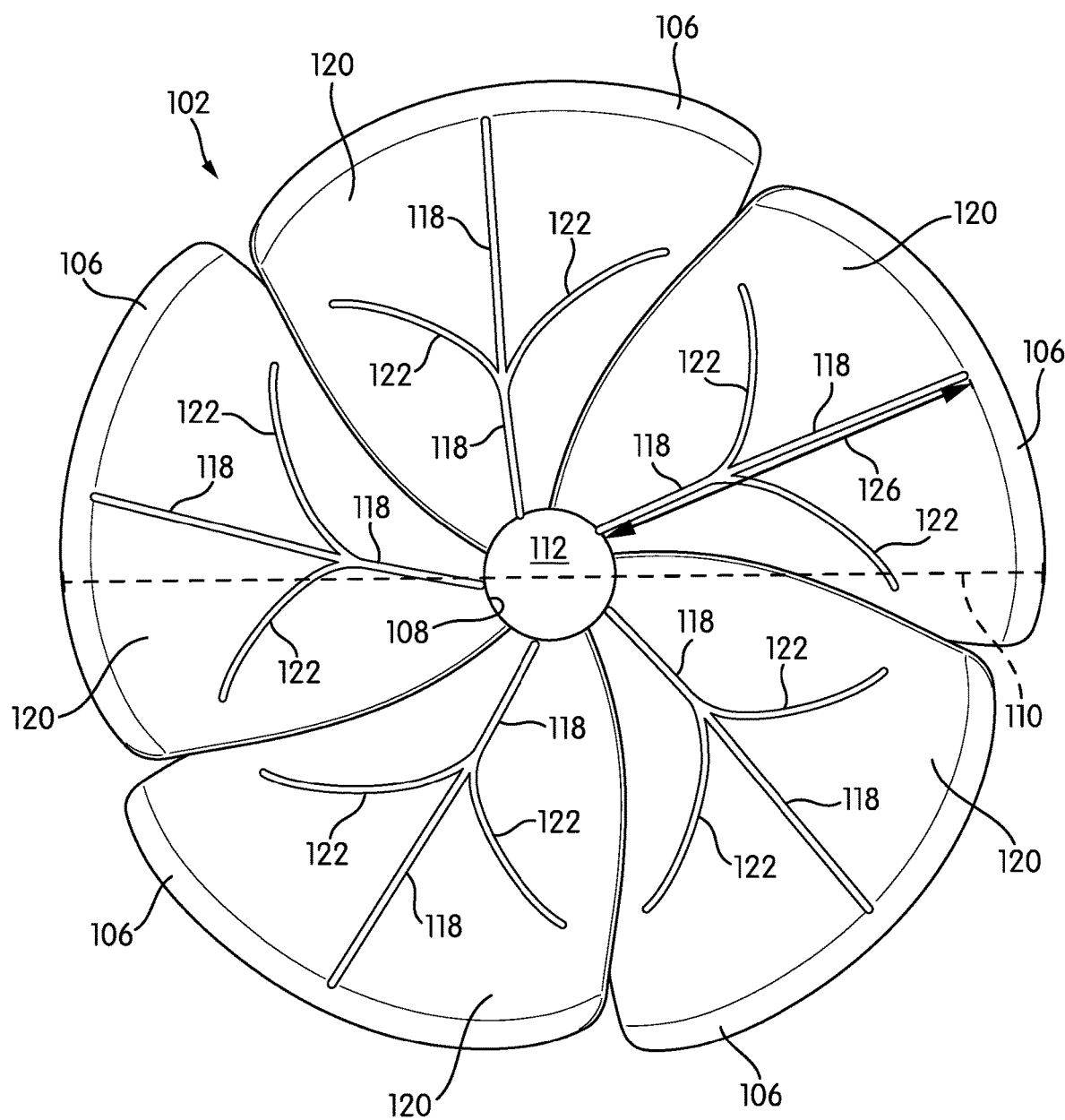
FIG. 1(b) is a top view of the irising drainage device of FIG. 1(a), according to an embodiment of the present disclosure.
Figure 2A:
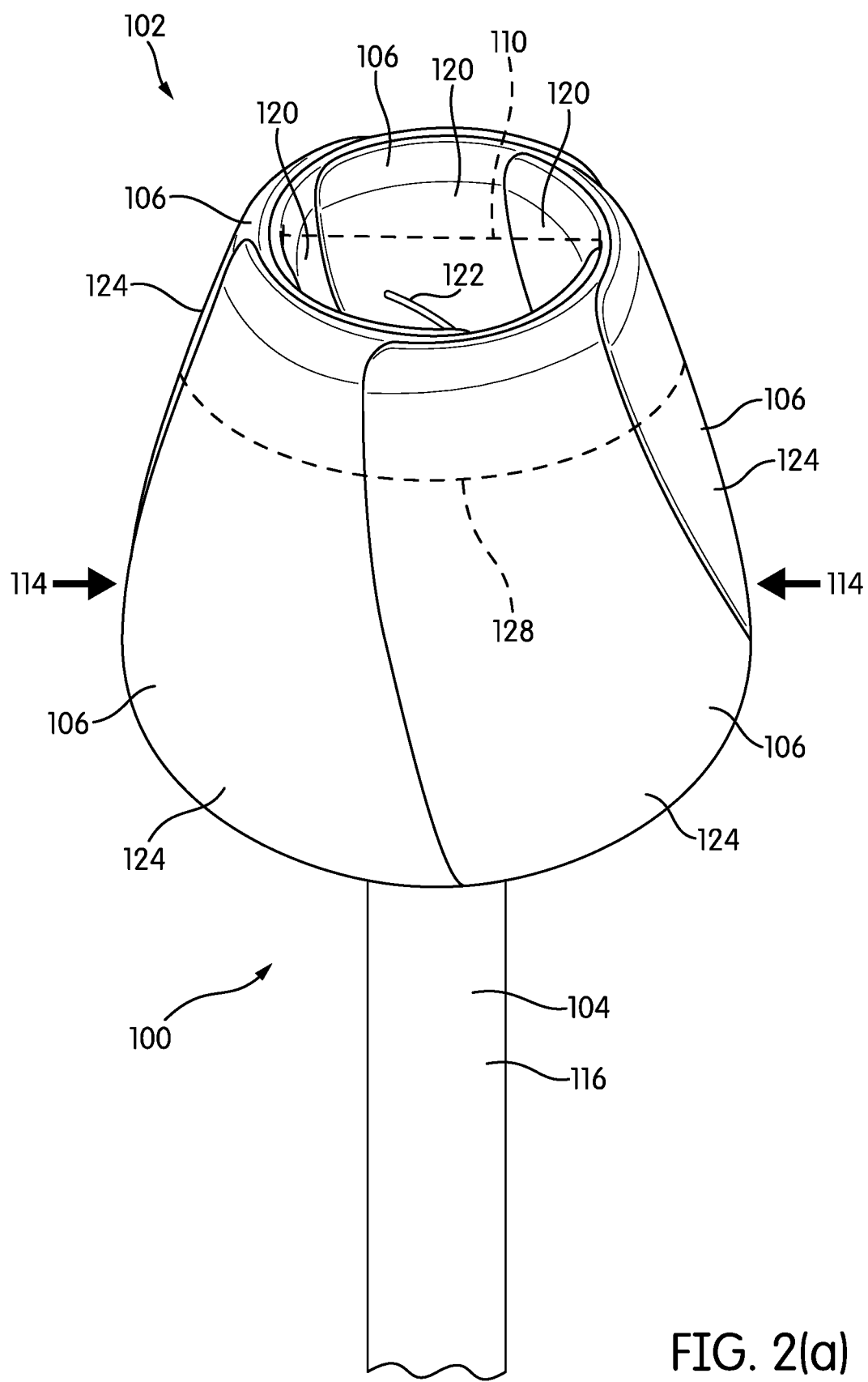
FIG. 2(a) is a perspective view of the irising drainage device of FIG. 1(a) in a narrowed conformation, according to an embodiment of the present disclosure.
Figure 2B:
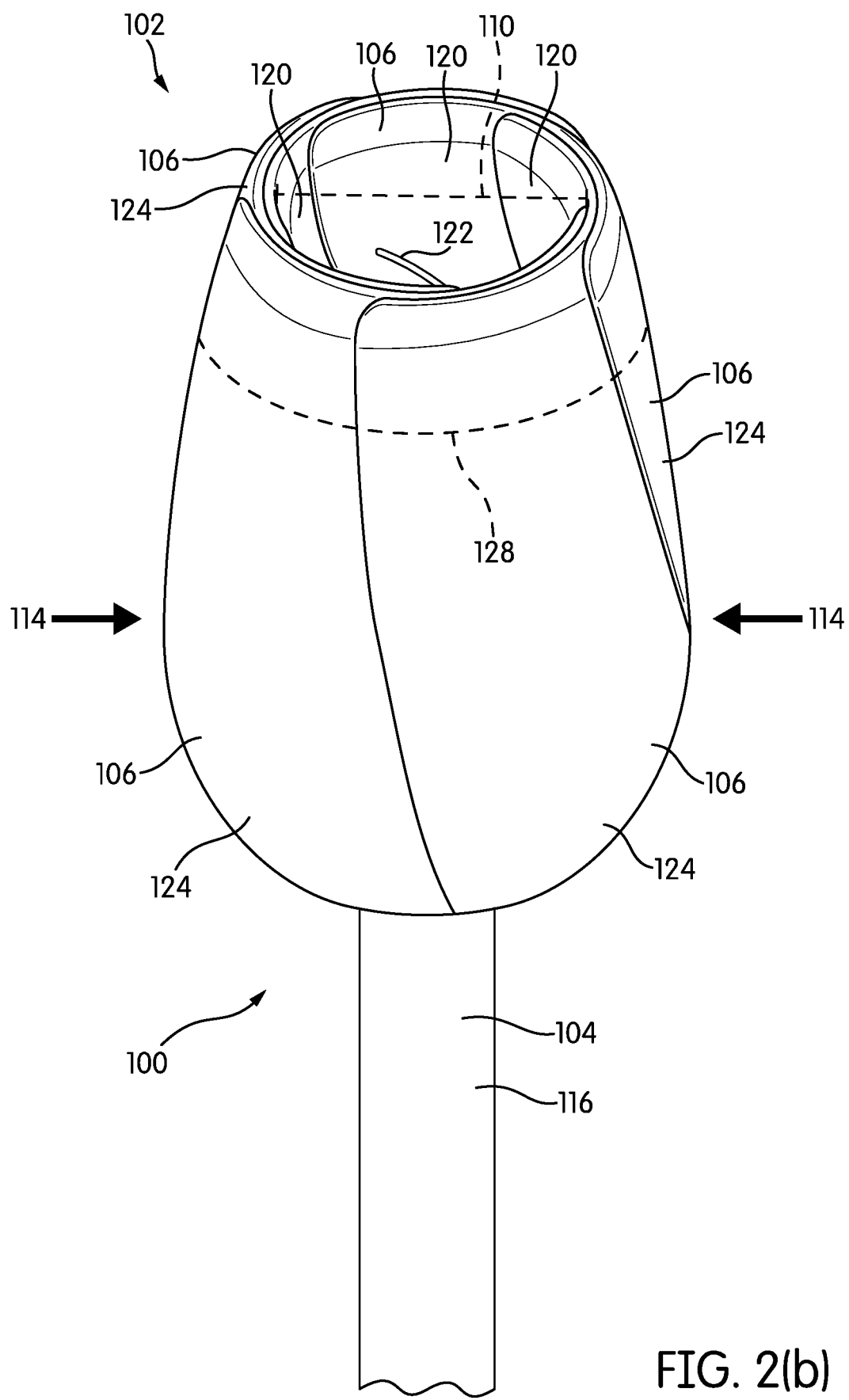
FIG. 2(b) is a perspective view of the irising drainage device of FIG. 1(a) in an alternative narrowed conformation, according to an embodiment of the present disclosure.
Figure 2C:
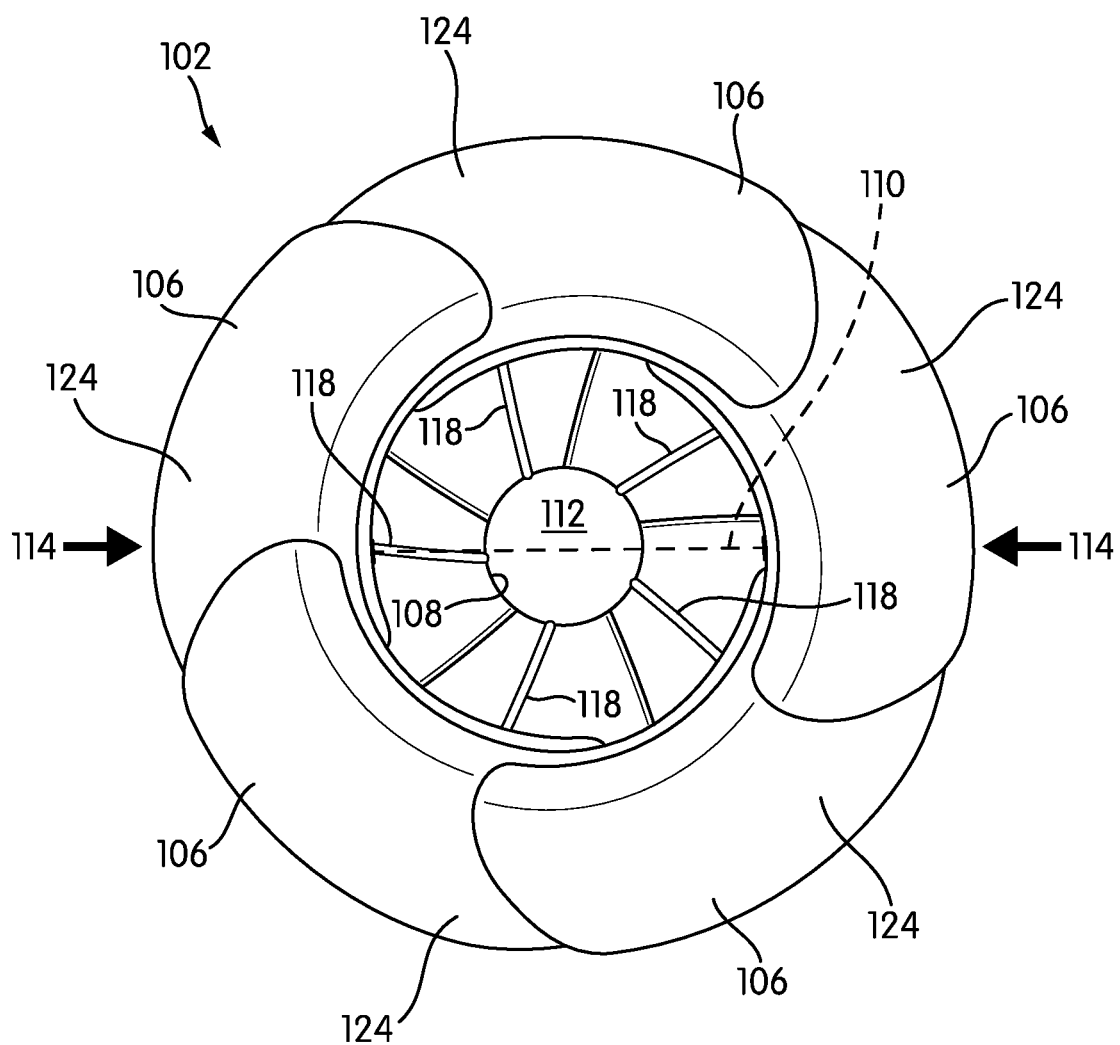
FIG. 2(c) is a top view of the irising drainage device of FIG. 2(a), according to an embodiment of the present disclosure.
Figure 3A:
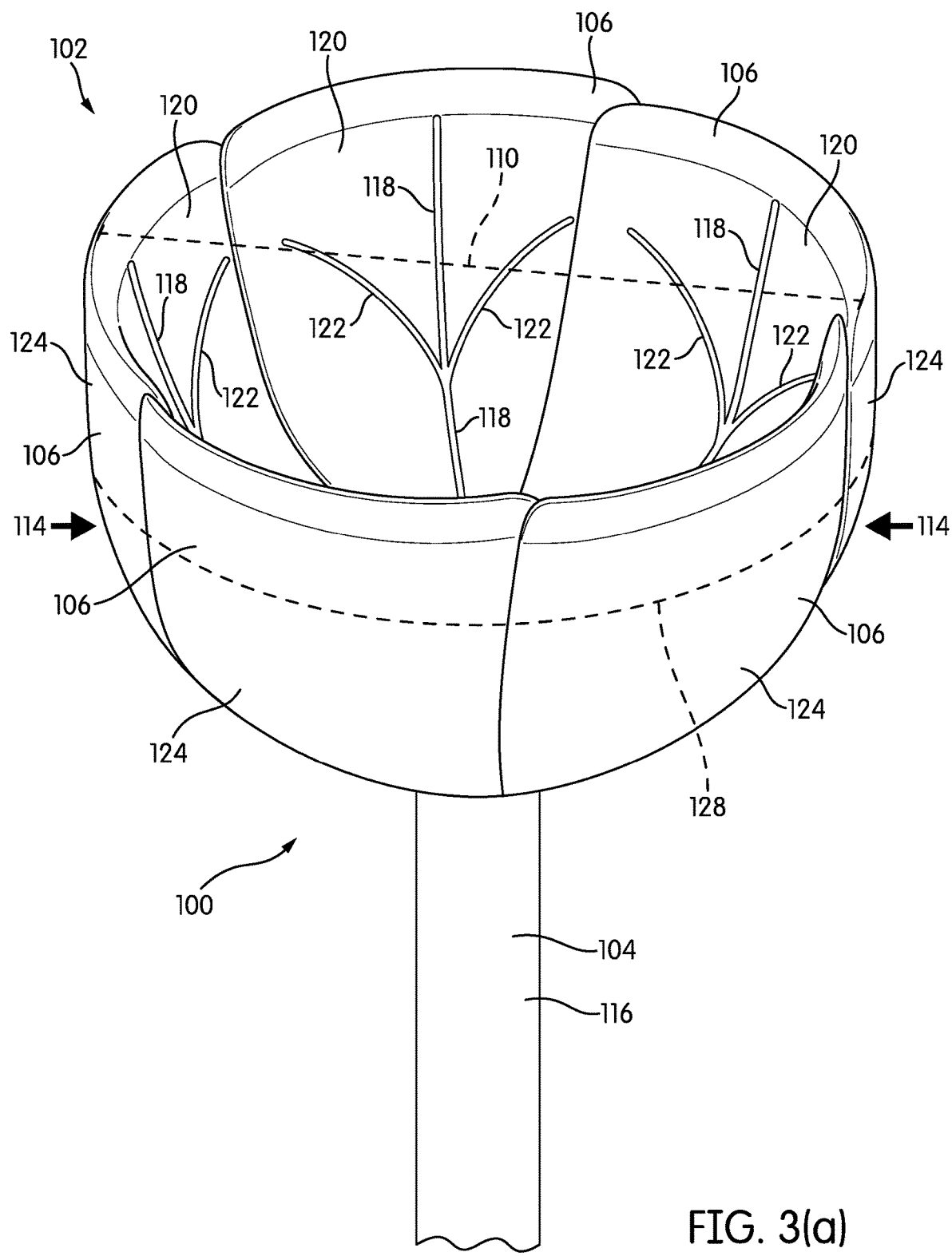
FIG. 3(a) is a perspective view of the irising drainage device of FIG. 1(a) in an intermediate conformation, according to an embodiment of the present disclosure.
Figure 3B:
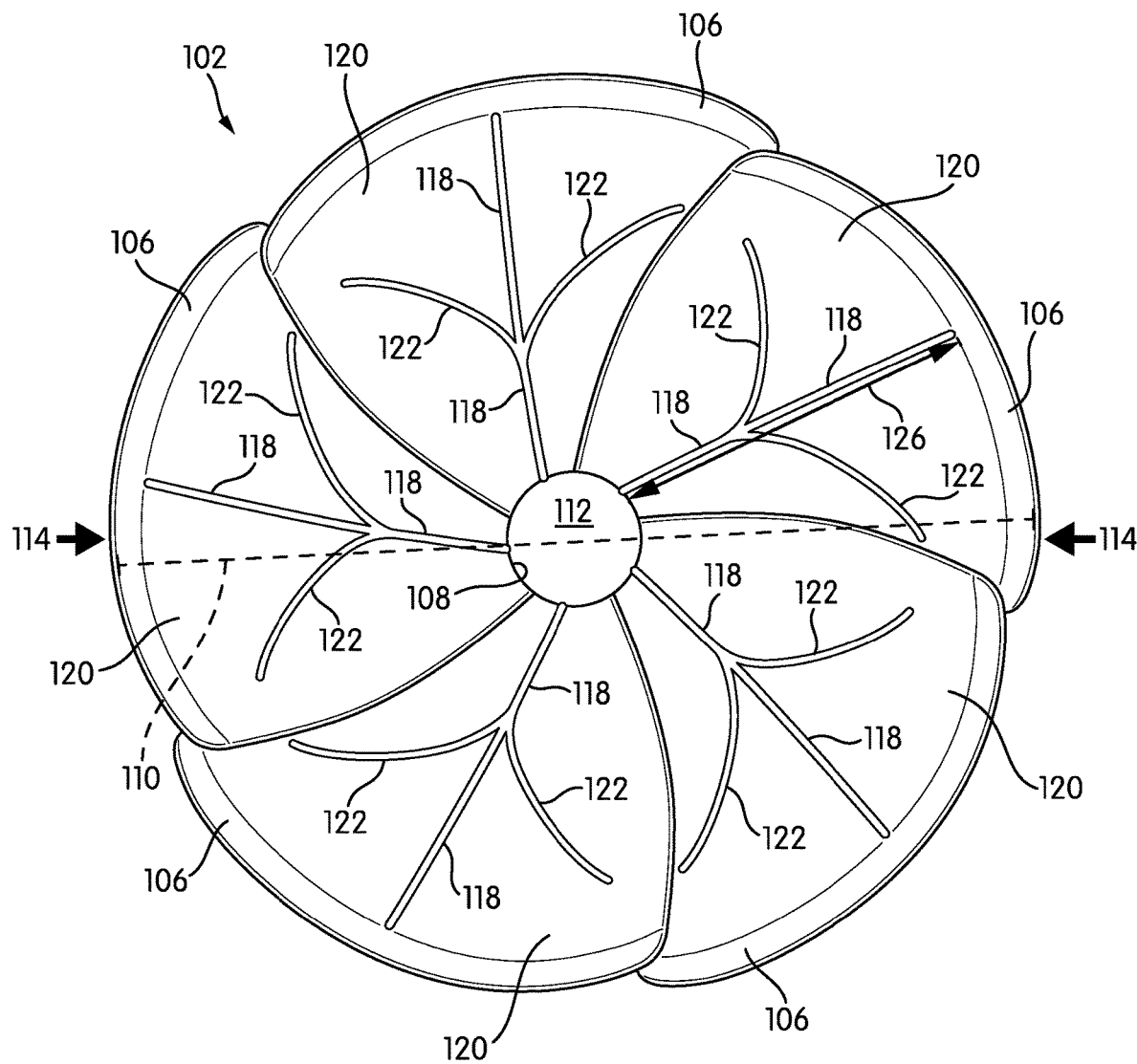
FIG. 3(b) is a top view of the irising drainage device of FIG. 3(a), according to an embodiment of the present disclosure.

In one embodiment, the irising collection funnel 102 has a base conformation of the plurality of overlapping petals in the absence of external stimuli, as shown in FIGS. 1(a) and 1(b). The irising collection funnel 102 is configured to elastically narrow in response to a radially inward pressure 114, with the plurality of overlapping petals 106 increasing in overlap with one another, as shown in FIGS. 2(a), 2(b), and 2(c). FIGS. 2(a) and 2(b) illustrate alternative narrowing configurations. In FIG. 2(a), a lower portion of the irising collection funnel 102 adjacent to the conduit 104 maintains a wide conformation which is understood to be somewhat more difficult to pass through an anus 406, but which may be appropriate where more rigid or thicker materials are desirable for greater strength and shape integrity. In contrast, in FIG. 2(b) the lower portion of the irising collection funnel 102 adjacent to the conduit 104 narrows significantly with the irising collection funnel 102 elongating accordingly for more facile passage of the irising collection funnel 102 through the anus 406 during insertion and removal procedures. In both embodiments, the irising collection funnel 102 expands back toward the base conformation with reduction of the radially inward pressure 114, with the plurality of overlapping petals 106 decreasing in overlap with one another, as shown in FIGS. 3(a) and 3(b).

By way of example, in one embodiment, wherein the irising collection device 100 is a rectal catheter, the irising collection funnel 102 elastically narrows in response to a radially inward pressure 114 as the irising collection funnel 102 passes through an anus 406, and then expands back partially toward the base confirmation after the irising collection funnel 102 passes through the anus 406 and enters into a rectal cavity 404, wherein the expansion of the plurality of overlapping petals 106 toward the base configuration is constrained by the walls of the rectal cavity 404. In a further embodiment, once the irising collection funnel 102 is disposed in the rectal cavity 404 and the plurality of overlapping petals 106 is constrained by the walls of the rectal cavity 404, the irising collection funnel 102 is configured to elastically contract and expand under the intermittent stimulation of peristalsis of the wall of the rectal cavity 404, and this elastic contraction and expansion of the irising collection funnel 102 rubs the plurality of overlapping petals against one another. The rubbing of the plurality of overlapping petals against one another under the influence of peristalsis may loosen effluent residuals clinging to the plurality of overlapping petals 106, cleaning the plurality of overlapping petals 106 and increasing passage of effluent through the annulus 108. It is noted than in an individual suffering from diarrhea, peristalsis is increased over typical bodily function, further increasing passage of effluent through the annulus 108.

For purposes of insertion of the irising collection funnel 102 through the anus 406 and into the rectal cavity 404, it is noted that the irising collection funnel 102 may be constrained or lubricated, or both for ease of insertion, patient comfort, and to prevent any of the plurality of overlapping petals 106 from being undesirably deformed or bent backward. Any suitable constraint or lubrication system may be used, including, but not limited to, a lubricated over-tube which is removed once the irising collection funnel 102 is in place. In some embodiments, an over-tube may be used for the removal of the irising collection funnel 102 from the rectal cavity 404 through the anus 406. In other embodiments, the removal of the irising collection funnel 102 from the rectal cavity 404 through the anus 406 may be performed by pulling the conduit 104, with or without a lubricant being applied.

The conduit 104 may have any suitable cross-sectional conformation, including, but not limited to, a circle, an ellipse, a triangle, a quadrilateral, a square, a rectangle, a pentagon, a hexagon, a heptagon, an octagon, or any combination thereof. In one embodiment, the conduit 104 is an elastomeric tube 116.

In one embodiment, the conduit 104 terminates at the annulus 108, and only the plurality of overlapping petals 106 expend beyond the annulus away from the conduit 104.

The plurality of overlapping petals 106 may include any suitable number of petals 106, including, but not limited to, at least three overlapping petals 106, alternatively at least four overlapping petals 106, alternatively at least five overlapping petals 106, alternatively at least six overlapping petals 106, alternatively at least seven overlapping petals 106, alternatively at least eight overlapping petals 106, alternatively at least nine overlapping petals 106, alternatively at least 10 overlapping petals.

Each of the plurality of overlapping petals 106 may be attached to the annulus 108, joined to the annulus 108, or integrally formed with the annulus 108. As used herein, "attached" indicates that a petal 106 is discontinuous from the annulus 108. Suitable attachments include, but are not limited to, a non-living hinge. As used herein, "joined" indicates that a petal 106 is continuous with, but not integrally formed with, the annulus 108, such that there is a melt joint, weld joint, braze joint, or adhesive joint between the petal 106 and the annulus 108. As used herein, "integrally formed with" indicates that the petal 106 and the annulus 108 are continuous with one another and that there is no joint, such that the distinction between the petal 106 and the annulus 108 is limited to geometry. The plurality of overlapping petals 106 may all be attached to the annulus 108, all be joined to the annulus 108, all be integrally formed with the annulus 108, or the plurality of overlapping petals 106 may include any suitable combination of individual petals 106 which are attached to the annulus 108, joined to the annulus 108, or integrally formed with the annulus 108.

The annulus 108 may be attached to the conduit 104, joined to the conduit 104, or integrally formed with the conduit 104. As used herein, "attached" indicates that the conduit 104 is discontinuous from the annulus 108. Suitable attachments include, but are not limited to, a snap fit. As used herein, "joined" indicates that the conduit 104 is continuous with, but not integrally formed with, the annulus 108, such that there is a melt joint, weld joint, braze joint, or adhesive joint between the conduit 104 and the annulus 108. As used herein, "integrally formed with" indicates that the conduit 104 and the annulus 108 are continuous with one another and that there is no joint, such that the distinction between the conduit 104 and the annulus 108 is limited to geometry.

Each of the plurality of overlapping petals 106 may be elastically deformable, inelastically deformable, or rigid. As used herein, "deformable" and "rigid" are differentiated by whether a pressure of more than 75 mmHg is required to deform a petal 106 (rigid) or whether a pressure of 75 mmHg or less will reform a petal 106 (deformable). The plurality of overlapping petals 106 may all be elastically deformable, all be inelastically deformable, all be rigid, or the plurality of overlapping petals 106 may include any suitable combination of individual petals 106 which are elastically deformable, inelastically deformable, or rigid.

Each of the plurality of overlapping petals 106 may elastically attach to the annulus 108 or rigidly attach to the annulus 108. The plurality of overlapping petals 106 may all elastically attach to the anulus 108, all rigidly attach to the annulus 108, or the plurality of overlapping petals 106 may include any suitable combinations of individual petals 106 which elastically attach to the anulus 108 or rigidly attach to the anulus 108.

Each of the plurality of overlapping petals 106 may include at least one primary support rib 118 extending radially outward along each of the plurality of overlapping petals 106 and exerting a radially outward biasing pressure on each of the plurality of overlapping petals 106. Each of the plurality of overlapping petals 106 may include any suitable number of primary support ribs 118, including, but not limited to, one primary support rib 118, two primary support ribs 118, three primary support ribs 118, or more than three primary support ribs 118. The at least one primary support rib 118 may be disposed on a radially inward side 120 of each of the plurality of overlapping petals 106 or be embedded within each of the plurality of overlapping petals 106. Each of the plurality of overlapping petals 106 has a petal material composition and the at least one primary support rib 118 has a rib material composition. The rib material composition may be identical to or distinct from the petal material composition. The at least one primary support rib 118 may include a spring. Suitable springs include, but are not limited to, torsion springs, flat springs, cantilever springs, leaf springs, or combinations thereof.

The petal material composition may include, but is not limited to, silicones, SILASTIC, rubbers, nylons, polyurethanes, polyethylene terephthalates, latex, thermoplastic elastomers, polyimides, polyesters, or combinations thereof. Any of the foregoing materials may be medical grade materials.

The plurality of overlapping petals 106 may have any suitable hardness, including, but not limited to, a hardness of Shore A hardness of between 1 and 50, alternatively between 1 and 10, alternatively between 5 and 15, alternatively between 10 and 20, alternatively between 15 and 25, alternatively between 20 and 30, alternatively between 25 and 35, alternatively between 30 and 40, alternatively between 35 and 45, alternatively between 40 and 50, or any combination or sub-range thereof.

Each petal 106 may have any suitable dimensions. Suitable lengths (measured from the annulus 108 to the furthest extent of the petal 106) include, but are not limited to, between 1 inch and 3 inches, alternatively between 1 inch and 1.5 inches, alternatively between 1.25 inches and 1.75 inches, alternatively between 1.5 inches and 2 inches, alternatively between 1.75 inches and 2.25 inches, alternatively between 2 inches and 2.5 inches, alternatively between 2.25 inches and 2.75 inches, alternatively between 2.5 inches and 3 inches, or any combination or sub-range thereof. Suitable widths (measured perpendicular to the length) at the widest portion of the petal 106 include, but are not limited to, between 0.5 inches and 3 inches, alternatively between 0.5 inch and 1 inch, alternatively between 0.75 inches and 1.25 inches, alternatively between 1 inch and 1.5 inches, alternatively between 1.25 inches and 1.75 inches, alternatively between 1.5 inches and 2 inches, alternatively between 1.75 inches and 2.25 inches, alternatively between 2 inches and 2.5 inches, alternatively between 2.25 inches and 2.75 inches, alternatively between 2.5 inches and 3 inches, or any combination or sub-range thereof. Suitable thicknesses (measure from the radially inward side 120 to the radially outward side 124) at the thickest portion of the petal 106 include, but are not limited to, between 0.05 inches and 0.075 inches, alternatively between 0.05 inch and 0.06 inches, alternatively between 0.055 inches and 0.065 inches, alternatively between 0.06 inches 0.07 inches, alternatively between 0.065 inches and 0.075 inches. The thickness may be uniform across the petal or may vary across the petal. The thickness of the petal 106 may change along the length of the petal 106, across the width of the petal 106, or both. The petal 106 may be thickest across the width of the petal 106 at the center of the petal 106 and decrease in thickness laterally to the edges of the petal 106, or the petal 106 may be thickest across the width of the petal 106 at the edges of the petal 106 and decrease in thickness toward the central of the petal 106. The petal 106 may be thickest along the length of the petal 106 at the center of the petal 106 and decrease in thickness toward the annulus 108 and toward the furthest extent of the petal 106 from the annulus 108, or the petal 106 may be thickest adjacent to the annulus 108 and decrease in thickness along the length of the petal 106 toward the furthest extent of the petal 106 from the annulus 108, or the petal may be thickest at the furthest extent of the petal 106 from the annulus 108 and decrease in thickness along the length of the petal 106 toward the anulus 108. The thickness of the petal 106 may vary in any combination of the afore-described changes in thickness along the length and across the width of the petal 106.

The rib material composition may include, but is not limited to, silicones, SILASTIC, rubbers, nylons, polyurethanes, polyethylene terephthalates, latex, thermoplastic elastomers, polyimides, polyesters, metals, steels, carbon steels, stainless steels, spring steels, titanium, shape-memory alloys, pseudoelastic alloys, or combinations thereof. Any of the foregoing materials may be medical grade materials.

Each of the plurality of overlapping petals 106 may further include a plurality of secondary support ribs 122 extending laterally from the at least one primary support rib 118 along a length 126 of the at least one primary support rib 118. The plurality of secondary support ribs 122 may be disposed on a radially inward side 120 of each of the plurality of overlapping petals 106 or be embedded within each of the plurality of overlapping petals 106. Each of the plurality of secondary support ribs 122 has a secondary rib material composition. The secondary rib material composition may be identical to or distinct from the rib material composition and may be identical to or distinct from the petal material composition. The plurality of secondary support ribs 122 may include a spring. Suitable springs include, but are not limited to, torsion springs, flat springs, cantilever springs, leaf springs, or combinations thereof.

The secondary rib material composition may include, but is not limited to, silicones, SILASTIC, rubbers, nylons, polyurethanes, polyethylene terephthalates, latex, thermoplastic elastomers, polyimides, polyesters, metals, steels, carbon steels, stainless steels, spring steels, titanium, shape-memory alloys, pseudoelastic alloys, or combinations thereof. Any of the foregoing materials may be medical grade materials.

Each of the plurality of overlapping petals 106 may include any suitable surface roughness on the radially inward side 120 of each of the plurality of overlapping petals 106 and any suitable surface roughness on the radially outward side 124 of each of the plurality of overlapping petals 106. In one embodiment, the surface roughness of the radially inward side 120 and radially outward side 124 of each of the plurality of overlapping petals 106 (excluding the presence of any primary support ribs 118 and secondary support ribs 122 disposed on the radially inward side 120) is the same. In another embodiment, the surface roughness of the radially inward side 120 is less than the surface roughness of the radially outward side 124 of each of the plurality of overlapping petals 106 (excluding the presence of any primary support ribs 118 and secondary support ribs 122 disposed on the radially inward side 120). Suitable surface roughness for the radially outward side 124 of each of the plurality of overlapping petals 106 includes, but is not limited to, surface roughness (Ra) less than 1.6 µm, alternatively less than 1.4 µm, alternatively less than 1.2 µm, alternatively less than 1.0 µm, alternatively less than 0.8 µm, alternatively less than 0.6 µm, alternatively less than 0.4 µm, alternatively less than 0.2 µm, alternatively less than 0.1 µm.

Referring to FIGS. 1(*a*), 1(*b*), 2(*a*), 2(*b*), 2(*c*), 3(*a*), and 3(*b*), in one embodiment the plurality of overlapping petals 106 sequentially overlap one another about a periphery 128 of the irising collection funnel 102.

Figure 5A:
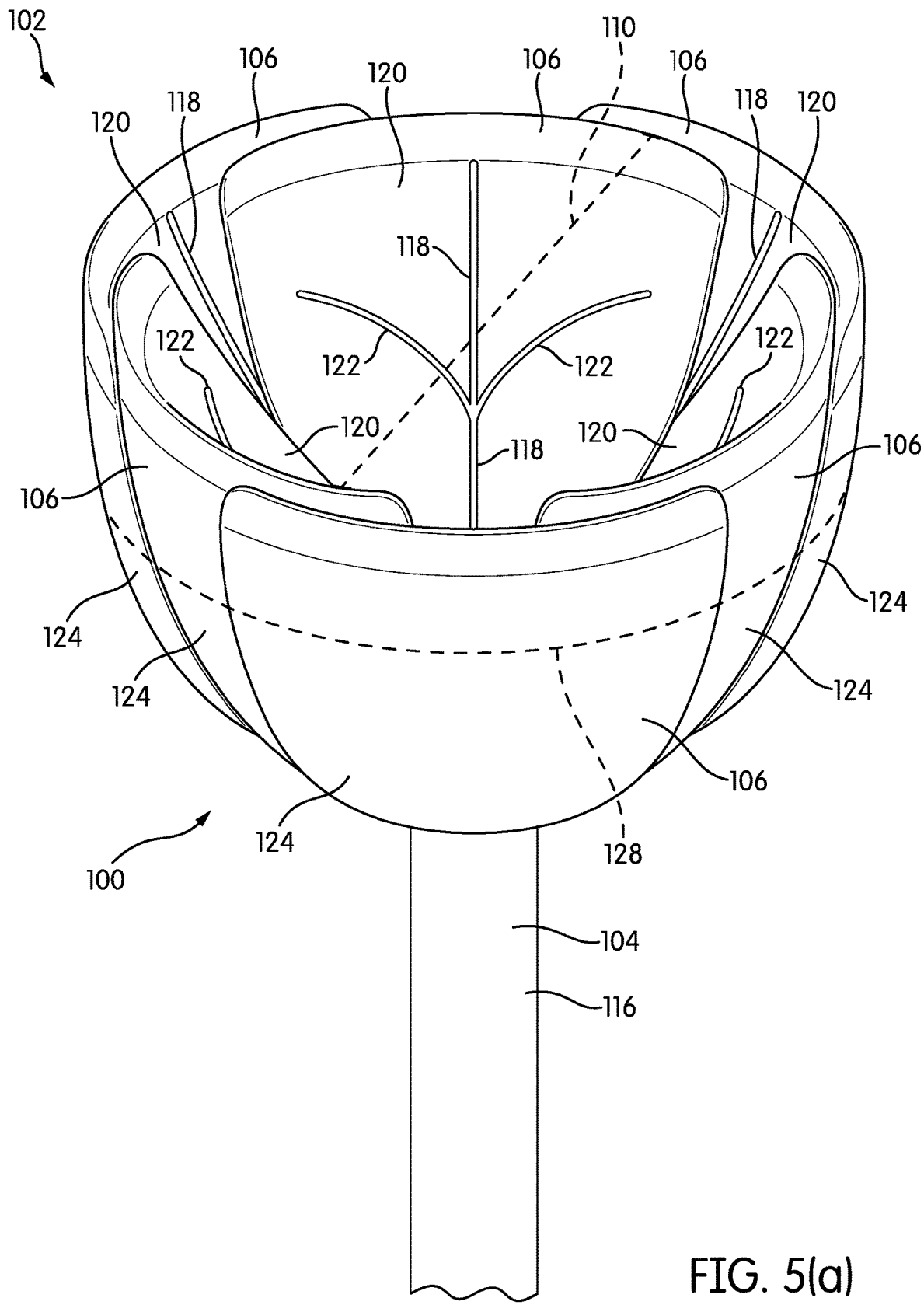
FIG. 5(a) is a perspective view of an irising drainage device in a base conformation with non-sequentially overlapping petals, according to an embodiment of the present disclosure.
Figure 5B:
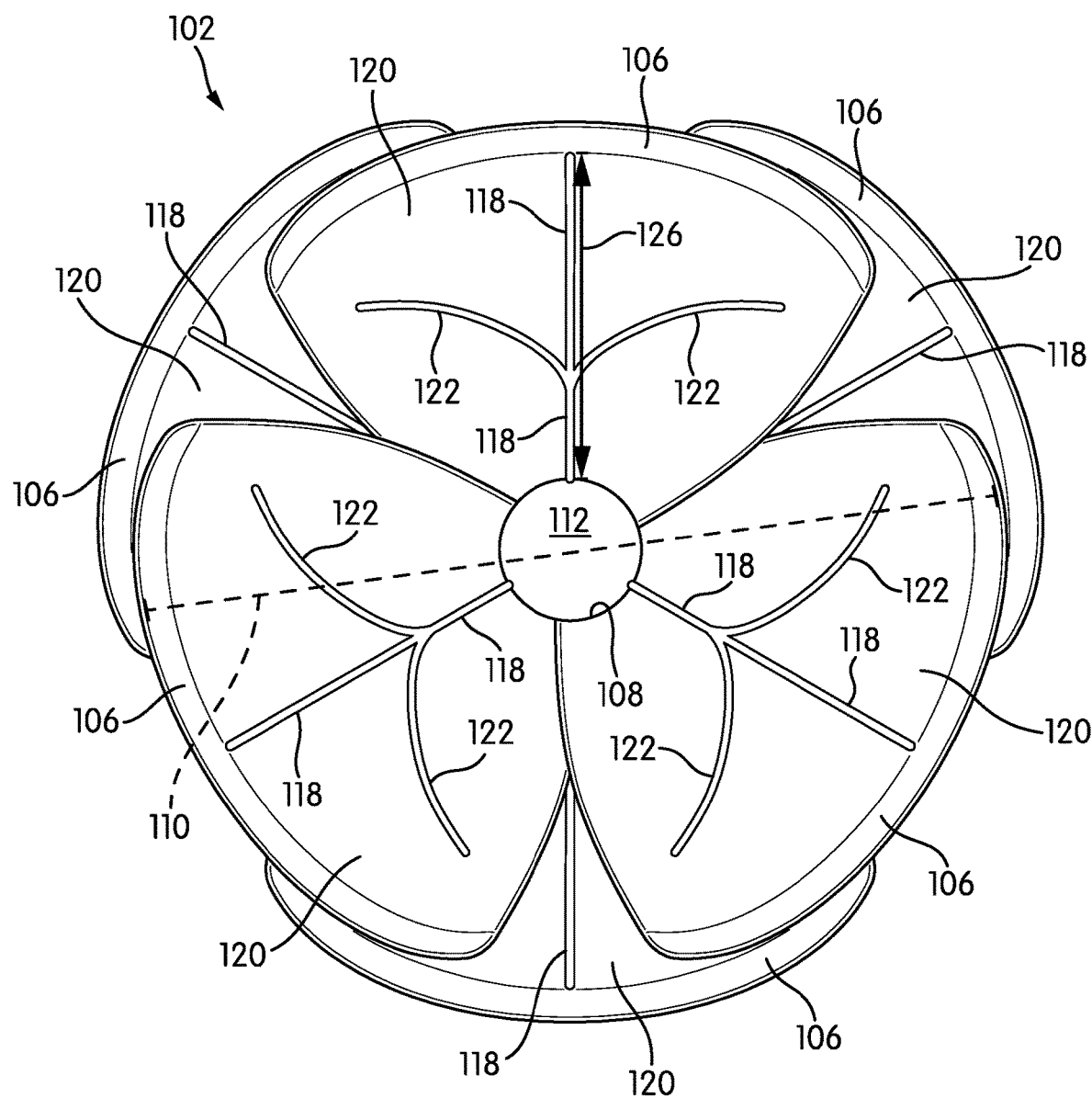
FIG. 5(b) is a top view of the irising drainage device of FIG. 5(a), according to an embodiment of the present disclosure.

Referring to FIGS. 5(*a*) and 5(*b*), in another embodiment the plurality of overlapping petals 106 non-sequentially overlap one another about a periphery 128 of the irising collection funnel 102.

Figure 6A:
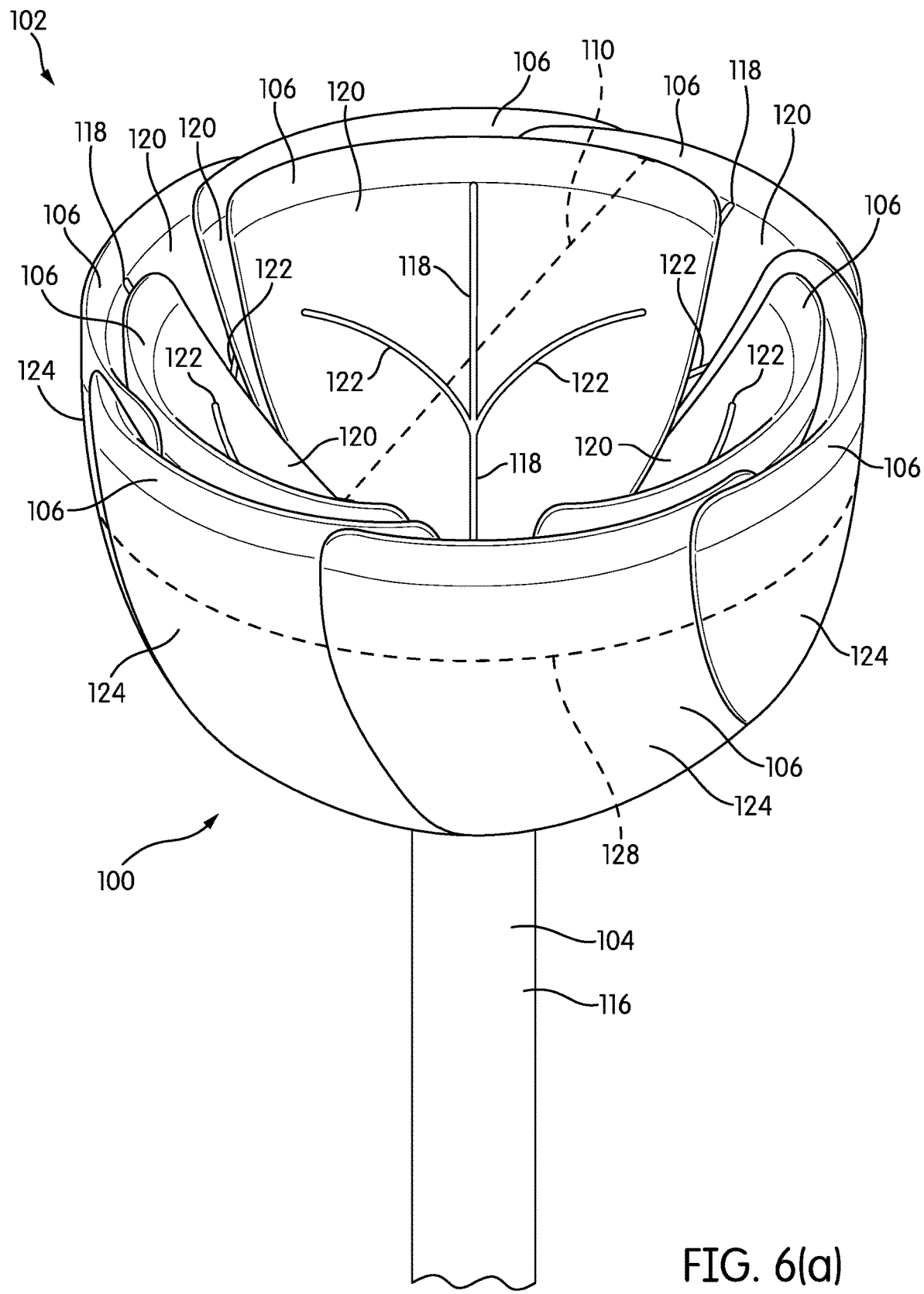
FIG. 6(a) is a perspective view of an irising drainage device having sequentially and non-sequentially overlapping petals, according to an embodiment of the present disclosure.
Figure 6B:
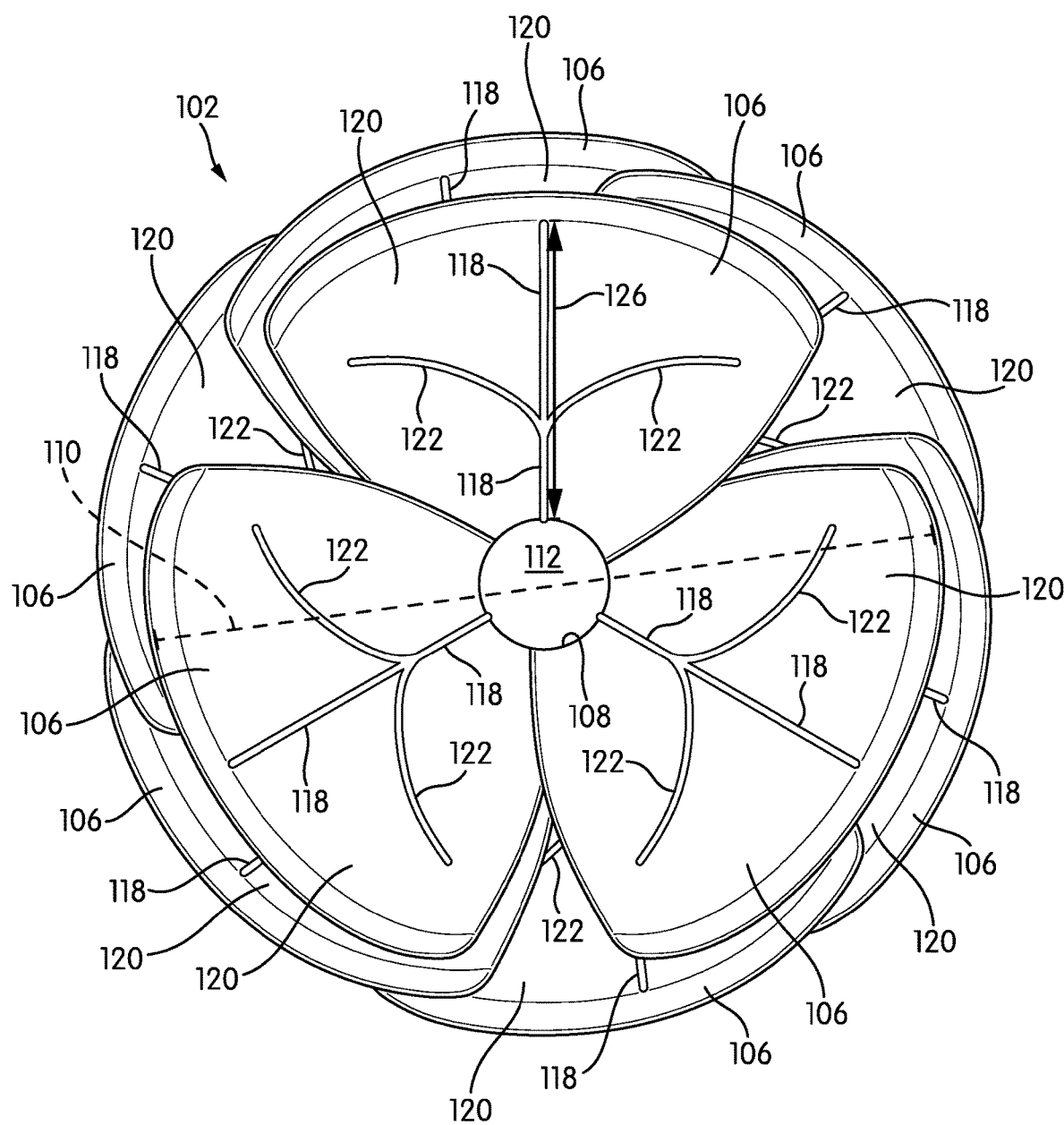
FIG. 6(b) is a top view of the irising drainage device of FIG. 6(a), according to an embodiment of the present disclosure.

Referring to FIGS. 6(*a*) and 6(*b*), in one embodiment, the plurality of overlapping petals 106 includes a first plurality of overlapping petals 602 which sequentially overlap one another about a periphery 128 of the irising collection funnel 102 and a second plurality of overlapping petals 604 which non-sequentially overlap one another about a periphery 128 of the irising collection funnel 102.

The irising collection funnel 102 may have any suitable material composition, including, but not limited to, silicones, SILASTIC, rubbers, nylons, polyurethanes, polyethylene terephthalates, latex, thermoplastic elastomers, polyimides, polyesters, or combinations thereof. Any of the foregoing materials may be medical grade materials.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An irising drainage device, comprising:
    an irising collection funnel including a plurality of overlapping petals extending from an annulus defining a central aperture; and
    a conduit extending from the annulus away from the irising collection funnel, the conduit having a lumen in fluid communication with the central aperture,
    wherein the irising drainage device is a rectal catheter.

2. The irising drainage device of claim 1, wherein the irising collection funnel has a base conformation of the plurality of overlapping petals in the absence of external stimuli and is configured to elastically narrow in response to a radially inward pressure, with the plurality of overlapping petals increasing in overlap with one another, and expand back toward the base conformation with reduction of the radially inward pressure, with the plurality of overlapping petals decreasing in overlap with one another.

3. The irising drainage device of claim 1, wherein the conduit is an elastomeric tube.

4. The irising drainage device of claim 1, wherein the plurality of overlapping petals includes at least three overlapping petals.

5. The irising drainage device of claim 1, wherein each of the plurality of overlapping petals is integrally formed with the annulus.

6. The irising drainage device of claim 1, wherein the annulus is integrally formed with the conduit.

7. The irising drainage device of claim 1, wherein each of the plurality of overlapping petals is elastically deformable.

8. The irising drainage device of claim 1, wherein each of the plurality of overlapping petals includes at least one primary support rib extending radially outward along each of the plurality of overlapping petals and exerting a radially outward biasing pressure on each of the plurality of overlapping petals.

9. The irising drainage device of claim 8, wherein the at least one primary support rib is disposed on a radially inward side of each of the plurality of overlapping petals.

10. The irising drainage device of claim 8, wherein each of the plurality of overlapping petals is formed of a petal material composition and the at least one primary support rib is formed of a rib material composition, and the petal material composition is compositionally distinct from the rib material composition.

11. The irising drainage device of claim 8, wherein each of the plurality of overlapping petals further includes a plurality of secondary support ribs extending laterally from the at least one primary support rib along a length of the at least one primary support rib.

12. The irising drainage device of claim 1, wherein each of the plurality of overlapping petals elastically attaches to the annulus.

13. The irising drainage device of claim 1, wherein the plurality of overlapping petals sequentially overlap one another about a periphery of the irising collection funnel.

14. The irising drainage device of claim 1, wherein the plurality of overlapping petals non-sequentially overlap one another about a periphery of the irising collection funnel.

15. The irising drainage device of claim 1, wherein the plurality of overlapping petals includes a first plurality of overlapping petals which sequentially overlap one another about a periphery of the irising collection funnel and a second plurality of overlapping petals which non-sequentially overlap one another about a periphery of the irising collection funnel.

16. The irising drainage device of claim 1, wherein the irising collection funnel has a material composition selected from the group consisting of silicones, rubbers, nylons, polyurethanes, polyethylene terephthalates, latex, thermoplastic elastomers, polyimides, polyesters, and combinations thereof.

17. An irising rectal catheter, comprising:
    an irising collection funnel including a plurality of overlapping elastically deformable petals extending from an annulus defining a central aperture; and
    an elastomeric tube extending from the central aperture away from the irising collection funnel, the elastomeric tube having a lumen in fluid communication with the central aperture,
    wherein:
        the irising collection funnel has a base conformation of the plurality of overlapping petals in the absence of external stimuli and is configured to elastically narrow in response to a radially inward pressure, with the plurality of overlapping petals increasing in overlap with one another, and expand back toward the base conformation with reduction of the radially inward pressure, with the plurality of overlapping petals decreasing in overlap with one another;

the plurality of elastically deformable overlapping petals, the annulus, and the elastomeric tube are integrally formed with one another;

the plurality of elastically deformable overlapping petals sequentially overlap one another about a periphery of the irising collection funnel; and when inserted into a patient, the irising collection funnel conforms spatially to a rectal cavity of the patient, and the elastomeric tube extends from the annulus which is disposed in the rectal cavity through an anus of the patient to an external environment.

18. An irising drainage device, comprising:

an irising collection funnel including a plurality of overlapping petals extending from an annulus defining a central aperture; and a conduit extending from the annulus away from the irising collection funnel, the conduit having a lumen in fluid communication with the central aperture, wherein each of the plurality of overlapping petals includes at least one primary support rib extending radially outward along each of the plurality of overlapping petals and exerting a radially outward biasing pressure on each of the plurality of overlapping petals, and wherein each of the plurality of overlapping petals further includes a plurality of secondary support ribs extending laterally from the at least one primary support rib along a length of the at least one primary support rib.

19. The irising drainage device of claim 18, wherein the irising drainage device is a catheter or a surgical drain.

20. An irising drainage device, comprising:

an irising collection funnel including a plurality of overlapping petals extending from an annulus defining a central aperture, the plurality of overlapping petals having radially inward sides and radially outward sides; and a conduit extending from the annulus away from the irising collection funnel, the conduit having a lumen in fluid communication with the central aperture, wherein the irising collection funnel is formed such that the plurality of petals elastically expand against a wall of a cavity in which the irising collection funnel is inserted with the radially outward sides of the plurality of overlapping petals contacting the wall of the cavity about a periphery of the irising collection funnel while the irising collection funnel collects fluid disposed in the cavity through the central aperture and transfers the fluid out from the cavity through the conduit.

* * * * *